(12) United States Patent
Tsuruta

(10) Patent No.: US 6,217,587 B1
(45) Date of Patent: *Apr. 17, 2001

(54) TREATMENT TOOL FOR AN ENDOSCOPE

(75) Inventor: Minoru Tsuruta, Hino (JP)

(73) Assignee: Olympus Optical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/140,821

(22) Filed: Aug. 26, 1998

(30) Foreign Application Priority Data

Oct. 9, 1997 (JP) .................................................... 9-277421

(51) Int. Cl.⁷ .................................................... A61B 17/24
(52) U.S. Cl. ............................... 606/113; 606/1; 600/104
(58) Field of Search ............................... 606/1, 110, 113, 606/114, 127, 128, 205–211; 600/104, 105, 153

(56) References Cited

U.S. PATENT DOCUMENTS

| | | |
|---|---|---|
| 4,046,150 | 9/1977 | Schwartz et al. . |
| 4,655,219 | 4/1987 | Petruzzi . |
| 5,201,740 * | 4/1993 | Nakao et al. ......................... 606/113 |
| 5,201,741 | 4/1993 | Dulebohn . |
| 5,496,330 | 3/1996 | Bates et al. . |
| 5,817,104 * | 10/1998 | Bilitz et al. .......................... 606/113 |

FOREIGN PATENT DOCUMENTS

| | | |
|---|---|---|
| 0 428 998 A1 | 5/1991 | (EP) . |
| 9-534 | 1/1997 | (JP) . |

* cited by examiner

Primary Examiner—Glenn K. Dawson
(74) Attorney, Agent, or Firm—Frishauf, Holtz, Goodman, Langer & Chick, P.C.

(57) ABSTRACT

The treatment tool for an endoscope has an operation portion including an operation portion body and a slider. The operation portion body has a proximal end portion provided with a ring-like finger engaging portion, and a grip portion is formed to be adjacent to the finger engaging portion. The slider has a pair of flanges for engaging a finger and a finger rest extending from the flange adjacent the rear end portion. An operator can insert his or her thumb of one hand into the ring-like finger engaging portion, and engages another finger of the same hand between the pair of flanges of the slider. The operation portion body and the slider can be relatively moved thereby. Otherwise, the operator can also relatively move the operation portion body and the slider by gripping the grip portion of the operation portion body on his or her palm of one hand and by engaging the thumb of the same hand on the finger rest of the slider shaped like a hood.

18 Claims, 6 Drawing Sheets

TREATMENT TOOL FOR AN ENDOSCOPE

BACKGROUND OF THE INVENTION

The present invention relates to a treatment tool for an endoscope, such as a high-frequency snare, forceps or the like, which is used under observation through an endoscope.

Japanese Patent Application KOKAI Publication No. 9-534 discloses such type of treatment tool for an endoscope. In that publication, the treatment tool is formed as a basket type forceps as shown in FIG. 14. The basket-type forceps comprises an operation wire inserted through a sheath 1 and basket wires 3 provided at a distal end portion of the operation wire. The basket wires 3 are moved forwards and backwards by operation through the hand operation section 2, and the basket wires 3 are thereby extended from the distal end portion of the sheath 1 or retracted thereinto. The hand operation portion 2 has an operation body 4 and a slider 5 slidable on the outer circumferential surface of the body. A pair of finger flanges 6 are formed on the slider 5 and a ring 7 is provided at a rear end portion of the operation body 4.

When the basket wire 3 is operated, an operator inserts his or her thumb into the ring 7 and holds and clamps the part of the slider 5 between the pair of flanges 6 with his or her forefinger and middle finger. In this manner, the operation body 4 can be moved forwards and backwards and the operation wire can also be thereby moved forwards and backwards through the sheath 1.

Meanwhile, U.S. Pat. No. 5,496,330 discloses an example of another type of treatment tool for an endoscope. In this type of treatment tool for an endoscope, a proximal end portion comprises a base portion which an operator can grasp on the palm of his or her hand and a slider projected sidewards such that the slider can be operated by the thumb of the same hand. A sheath is connected with the slider. In this manner, the operator can move forwards and backwards the slider by the thumb while holding the base section on the palm.

In case of the treatment tool for an endoscope shown in FIG. 14, a thumb is inserted into the ring 7 of the operation body 4. Therefore, an operator scarcely drops the operation portion after the operator grasps the operation portion. Accordingly, the operator can reliably operate the tool.

However, since this type of treatment tool for an endoscope is operated by only three fingers, several operators cannot have a clear feeling of operating the tool and feel unreliable on it. When the basket wires 3 are extended from or retracted into the distal end of the sheath 1, the operation wire can be moved without moving the sheath 1. Therefore, to grasp a stone at a predetermined position, the basket wire 3 must be contracted while drawing back the basket wire 3 connected to the distal end of the operation wire, into the sheath. Therefore, the basket wire 3 moves in relation to the stone, making it difficult to grasp the stone.

Meanwhile, the endoscope treatment tool described in the U.S. Pat. No. 5,496,330 is operated by the entire of one hand, the operator can easily have a clear feeling of operating the tool. However, there is an operational drawback that it is difficult to apply a handling force to move backwards the slider to tighten the basket wires. In addition, the operator feels a fear that the operation portion may slip on his or her hand and may drop the tool.

Thus, two operation methods have been adopted in a conventional treatment tool for and endoscope, and each of the methods provides both of merits and demerits. Which of the methods is better depends on the operator's choice and cannot be determined definitely. However, it is not economical to prepare both treatment tools adopting different operation methods for the sake of one certain medical operation or for every operator, and management of equipment stocks is complicated. If there occurs a situation that one of the operation methods had better be changed to the other during one medical operation, the conventional treatment tools for an endoscope cannot deal with such a situation because each of the conventional treatment tools is limited to only one of the above-described methods.

BRIEF SUMMARY OF THE INVENTION

The present invention has been made in view of the above problems, and has an object of providing an treatment tool for an endoscope, by which an appropriate operation method can be freely selected in accordance with an operator's choice about operation methods or a situation of a medical operation, so that an excellent operation ability is provided.

According an aspect of the present invention, there is provided a treatment tool used under observation through an endoscope and comprising a treatment portion at a top end portion of the treatment tool, an insertion portion for inserting the treatment portion into a body cavity, an operation portion provided in a proximal end portion of the insertion portion, by which an operator can drive and operate the treatment portion from outside of a human body, the treatment tool comprising: first and second operation members each having a distal end portion and a proximal end portion and being movable relatively each other, the operation members forming the operation portion to be operated by the operator; a first finger engaging portion formed at the rear end portion of the first operation member and having a ring-like shape into which the operator can insert a thumb; a grip portion formed at the first operation member, to be adjacent to the first finger engaging portion, such that the operator can grasp the grip portion on a palm; a second finger engaging portion formed at the second operation member, such that the operator can engages the second finger engaging portion with at least one finger of the hand which includes the thumb engaging the first finger engaging portion; and a third finger engaging portion formed at the second operation member, such that the operator can engage the third finger engaging portion with the thumb of the hand grasping the grip portion, wherein selection can be made from a first drive operation of relatively moving the first and second operation members by the first and second finger engaging portions, and a second drive operation of relatively moving the first and second operation members by the grip portion and the third finger engaging portion.

According to another aspect of the present invention there is provided a treatment tool used under observation by an endoscope, comprising a sheath having a distal end portion to be inserted into a body cavity, an operation wire inserted in the sheath such that the operation wire is movable in an axial direction, an operation portion by which an operator relatively moves the sheath and the operation wire, and a treatment portion provided at a distal end portion of the operation wire, which can be driven and moved between a position where the treatment portion is extended from a distal end of the sheath and a position where the treatment portion is retracted into the sheath, through the operation portion by the operator, the treatment tool comprising: first and second operation members each having a distal end portion and a proximal end portion and being movable relatively each other, one of the first and second operation members being connected to the sheath and another one of the first and second operation members being connected to the operation wire, such that the first and second operation members form the operation portion to be operated by the operator; a first finger engaging portion formed at the rear end portion of the first operation member and having a ring-like shape into which the operator can insert a thumb; a grip portion formed at the first operation member, to be adjacent to the first finger engaging portion, such that the operator can grasp the grip portion on a palm; a second finger engaging portion formed at the second operation member, such that the operator can engage the second finger engaging portion with at least one finger of the hand which has the thumb engaging the first finger engaging portion; a third finger engaging portion formed at the second operation member, such that the operator can engage the third finger-hang portion with the thumb of the hand grasping the grip portion; and wherein selection can be made from a first drive operation of relatively moving the first and second operation members by the first and second finger engaging portions, and a second drive operation of relatively moving the first and second operation members by the grip portion and the third finger engaging portion.

Thus, in any of the treatment tools for an endoscope according to the aspects of the present invention, an appropriate operation method can be freely selected for making a treatment in accordance with an operator's choice or the situation of a medical operation or the like, so that the operation ability is very high.

Preferably the second finger engaging portion has a pair of flanges provided at the second operation member. The third finger-hang portion is preferably formed at one of the pair of flanges. Further, the third finger engaging portion is preferably provided closer to the grip portion than the second finger engaging portion.

If the third finger engaging portion has a hood portion extending toward the grip portion from one of the flanges that is closer to the grip portion, this position close to the palm allows the operator to operate the tool with a large stroke.

It is preferable that the first and second operation members respectively have substantially flat side surface portions opposed to each other, by which the operation portion is entirely formed into a substantially flat shape. In this case, the tool can be constructed in a compact structure.

Preferably, the second finger-hang portion has a pair of flanges formed at the second operation member, and the pair of flanges respectively have substantially flat side surface portions opposed to each other.

If the grip portion has an overhang portion on which a finger of a gripping hand hangs, a grip portion can be formed to be easy to grip. If the overhang portion has a wavy outer shape, positioning of a hand can be carried out with ease. Further, if the grip portion has a predetermined size in a lateral direction and if the overhang portion has a size in the lateral direction, which is smaller than the predetermined size of the grip portion, the treatment tool can be formed to be compact and easy to grip.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments give below, serve to explain the principles of the invention.

In the following, detailed explanation will be made of a treatment tool for an endoscope according to an embodiment of the present invention, with reference to the attached drawings.

DETAILED DESCRIPTION OF THE INVENTION

First Embodiment

The first embodiment of the present invention will be explained with reference to FIGS. 1 to 10. The treatment tool for an endoscope according to the first embodiment is a stone collection forceps used in combination with an urologic endoscope or a pancreatic and gallbladder endoscope.

Figure 1:
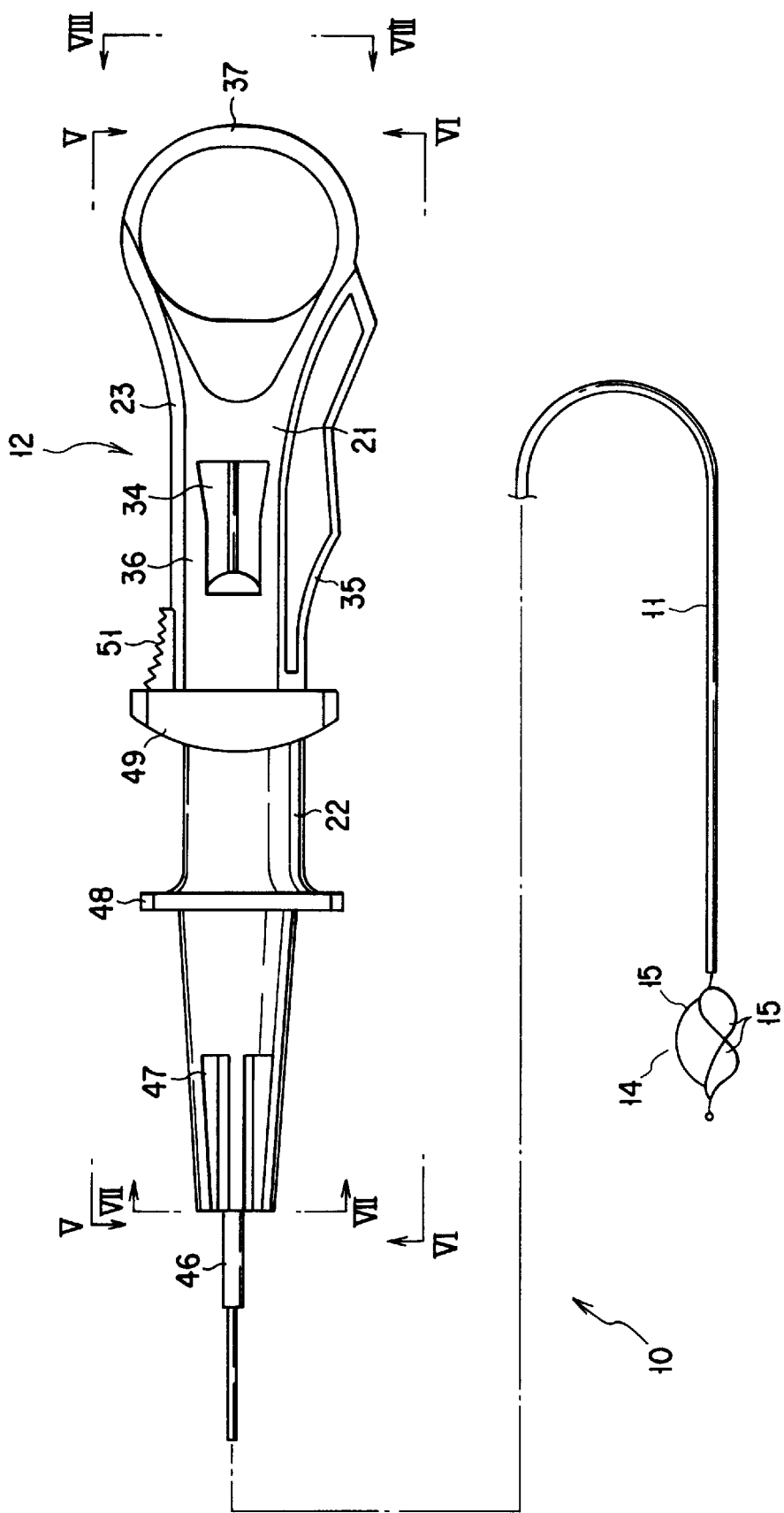
FIG. 1 is a side view of a forceps for an endoscope according to a first embodiment of the present invention.

FIG. 1 schematically shows the whole of the forceps 10. The forceps 10 comprises a flexible sheath 11 which forms an insertion portion inserted into a body cavity of a patient through a channel of an endoscope not shown. The sheath 11 is formed in a tubular shape made of a material such as FEP, PTFE, polyimide, or the like. An operation portion 12 is provided at a proximal end portion of the sheath 11. An operation wire 13 is inserted through the sheath 11.

A basket portion (or grasp portion) 14 as a treatment portion is provided at the distal end portion of the operation wire 13. The basket portion 14 is formed of a plurality of elastic wires 15 and can freely move forwards and backwards between a position where the portion 14 is projected or extended from the top end portion of the sheath 11 and a position where the portion 14 is retracted in the sheath 1. The elastic wires 15 are elastically expanded at the position where they are extended from the sheath 1 and can be contracted gradually as they are retracted into the sheath 1. Therefore, the basket portion 14 is expanded to a large diameter and can internally take in a stone, calculus or the like, when the basket portion 14 is extended from the distal end portion of the sheath 11 by the operation wire 13. Once the basket portion 14 is retracted into the sheath 11, the portion 14 thus retracted is contracted and can grasp the stone by the elastic wires 15.

The operation portion 12 comprises an operation body 21 as a first operation member and a slider 22 as a second operation member, for example. The operation body 21 of the present embodiment is formed by combining a support member 23 and a guide member 24 with each other. The guide member 24 includes a fitting portion 25 to be fitted onto the support member 23, and a guide portion 38 described later, for guiding the slide member 22.

An axial hole 26 in which the fitting portion 25 is engaged is formed at the distal end portion of the support member 23. The axial hole 26 has a stepped portion 27 at an intermediate portion along the axial direction, and the diameter of the stepped portion 27 is decreased at the side of the rear end portion. In matching with the hole 26, a stepped portion 27 is formed at an intermediate portion in the axial direction, and the diameter of the stepped portion is also decreased at the side of the rear end portion.

Figure 3:
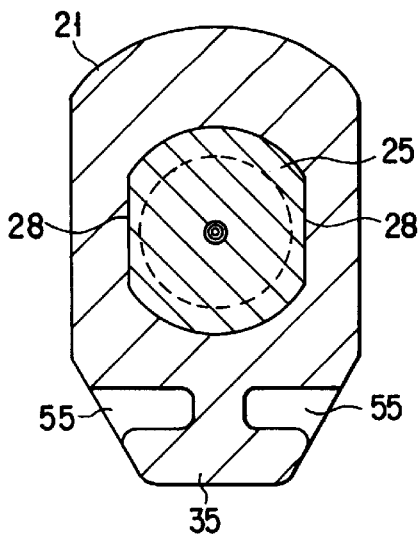
FIG. 3 is a transverse cross-sectional view of the portion along a line III—III shown in FIG. 2.

Particularly, as shown in FIG. 3, each of the axial hole 26 of the support member 23 and the fitting portion 25 of the guide member 24 are formed such that portions in the rear end sides of the stepped portions 27 are formed to have circular cross-sections and the other portions in the front end sides have substantially flat side surfaces 28 opposed to each other. Further, the flat side surfaces of the axial hole 26 and the fitting portion 25 are brought into contact with each other, thereby preventing the guide member 24 from being rotated in relation to the support member 23 around the axis thereof. A through-window 34 extending in the lateral direction and also functioning as a lightening hole is formed at an intermediate portion of the support member 23.

Figure 4:
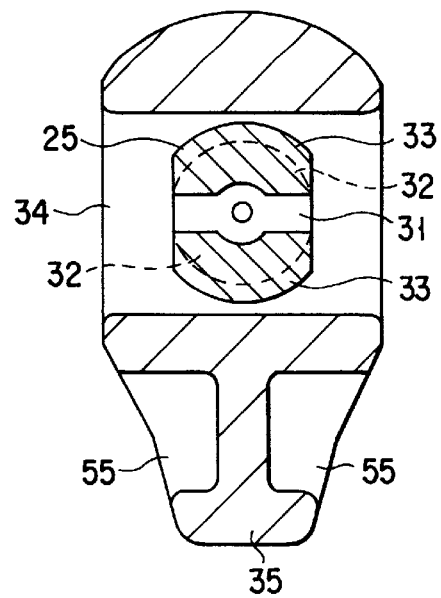
FIG. 4 is a transverse cross-sectional view of the portion along a line IV—IV shown in FIG. 2.
Figure 5:
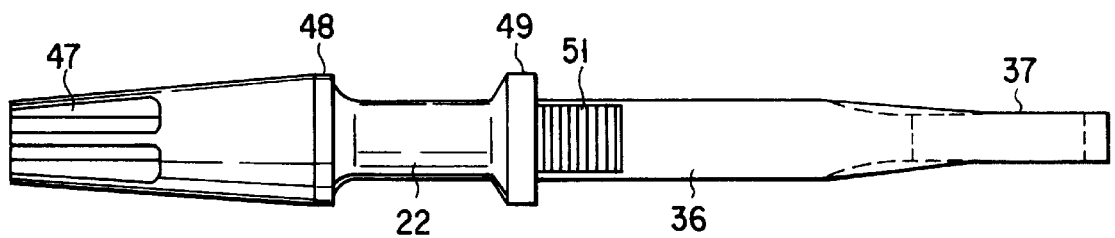
FIG. 5 is a plan view showing an operation portion of the forceps according to the first embodiment.
Figure 6:
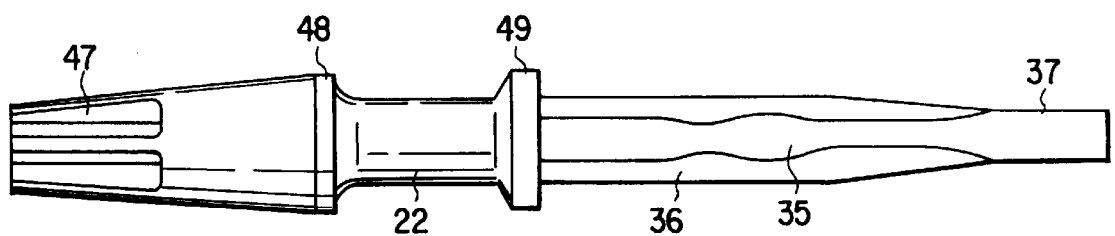
FIG. 6 is a bottom view showing an operation portion of the forceps according to the first embodiment.
Figure 7:
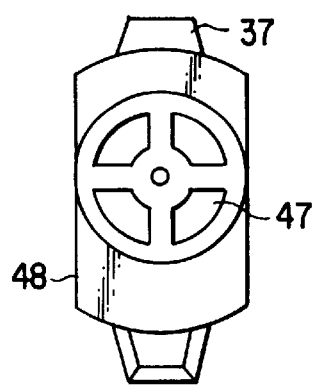
FIG. 7 is a front view showing an operation portion of the forceps according to the first embodiment.
Figure 8:
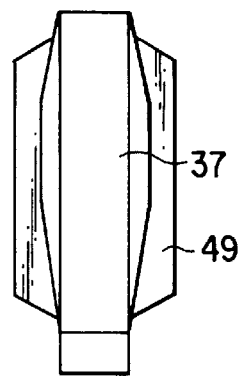
FIG. 8 is a rear view showing an operation portion of the forceps according to the first embodiment.

Further, as shown in FIG. 4, the fitting portion 25 of the guide member 24 has a slit-like expanding slot 31. The expanding slot 31 forms upper and lower arm portions 32 extending in the axial direction in the small-diameter portion of the fitting portion 25. Latch claws 33 are projected upwards and downwards from the rear end portions of the arm portions 32. The arm portions 32 can be elastically bent in the direction in which the slit 31 is closed, so that the latch claws 33 can be inserted through the small-diameter portion of the axial hole 26.

In case of connecting the support member 23 with the guide member 24, the fitting portion 25 is inserted into the axial hole 26. When the latch claws 33 are brought into contact with the stepped portion 27 of the axial hole 26, the two arm portions 32 are elastically bent in the direction in which the arms come close to each other, by curved surfaces or slanting surfaces of the end surfaces of the stepped portion 27 and the latch claws 33, so that the latch claws 33 are fitted into the small diameter portion of the axial hole 26. Further, the fitting portion 25 is moved through the axial hole 26 toward the rear end portion, and the stepped portions 27 of the fitting portion 25 and the axial hole 26 are brought into contact with each other. Then, the latch claws 33 are engaged with the engaging surface formed between the axial hole 26 and the through-window 34. Therefore, relative movement of the support member 23 and the guide member 24 in the axial direction can be prevented.

The support member 23 has a protruding portion 35 suspended downwards and the lower edge portion of the protruding portion 35 has an wavy outer shape which facilitates positioning of a hand. Also, the lower edge portion of the protruding portion 35 is formed in a scalloped edge shape corresponding to fingers of an operator, and is also capable of stopping slippage of fingers of the operator. The portion of the member 23 including the protruding portion 35 forms a grip portion 36 which the operator can grasp on his or her palm. A ring-like portion 37 is formed to be adjacent to the grip portion 36, at the rear end portion of the support member 23. The operator can insert his or her thumb into the portion 37.

Figure 2:
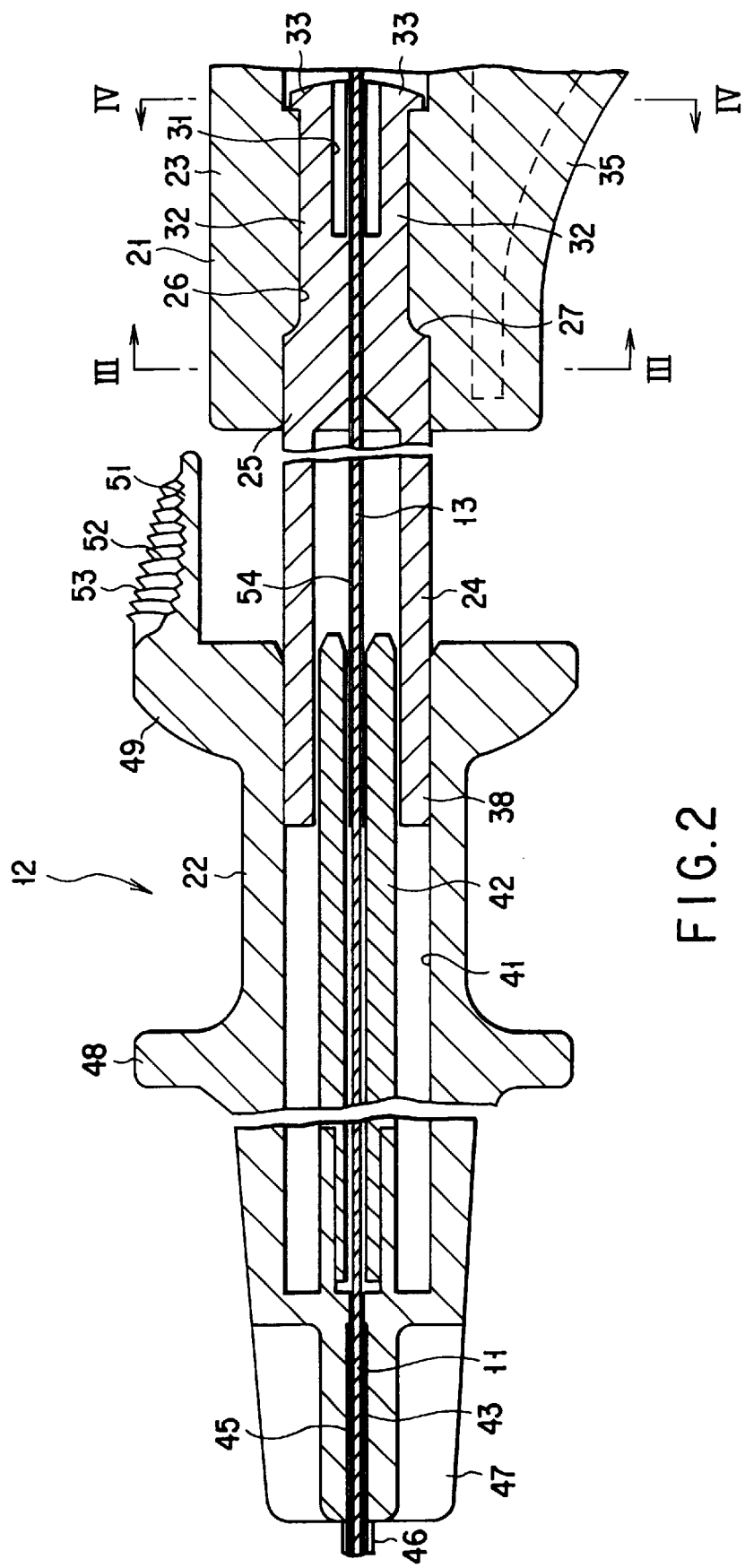
FIG. 2 is a longitudinal cross-sectional view showing an operation portion of the forceps according to the first embodiment.

As shown in FIG. 2, the guide portion 38 has a cylindrical structure formed at the distal end portion of the guide member 24. The guide portion 38 is slidably inserted in the guide hole 41 formed along the axial direction of the slider 22. The guide portion 38 is defined by substantially flat side surfaces 28 extended from the fitting portion 25 and opposed to each other. The guide hole 41 is also defined by substantially flat side surfaces (not shown) corresponding to the side surfaces 28 of the guide portion 38. Therefore, the guide portion 38, i.e., the guide member 24 or the operation body 21 is prevented from rotating in relation to the guide hole 41, i.e., the slider 22, around the axial line thereof.

A guide sleeve 42 arranged coaxially with the guide hole 41 is provided in the guide hole 41. The guide sleeve 42 is made of a material different from that of the slider 22 and is connected with the slider 22 at the distal end portion thereof.

At the center of the top end portion of the slider 22, a fitting hole 43 is opened to the top end side (or the left side in FIG. 2). The rear end of the sheath 11 is fixedly connected to the hole 43. In the present embodiment, a pipe member 45 is engaged on the rear end portion of the sheath 11. The rear end portions of both the sheath 11 and the pipe member 45 are inserted into the hole 43 and are fixed by adhesion or the like. A portion of the pipe member 45 which is projected from the hole 43 and the proximal end portion of he sheath 11 are covered with a anti-bending tube 46.

A rib 47 is formed on the outer circumference of the distal end portion of the slider 22. A pair of front and rear finger flanges (or finger engaging portions) 48 and 49 are integrally formed on the outer circumference of the rear end portion of the slider 22. In addition, a finger rest 51 is integrally formed at an upper end portion of the flange 49 close to the support member 23. The finger rest 51 is formed of a hood portion extending toward the rear end portion, and particularly, toward the grip portion 36. A concave portion 52 fitted with the thick of a thumb to be set thereon is formed on the upper surface of the finger rest 51. A knurled slip stopper 53 is formed on the surface of the concave portion 52 to prevent slippage.

Meanwhile, in the operation portion 12, the operation wire 13 extends through the guide sleeve 42 from the pipe member 45, penetrates through the guide member 24 of the operation body 21 to the support member 23, and is fixed to the support member 23. The operation wire portion penetrating through the guide member 24 is equipped with a reinforcement pipe 54 attached to the guide member 24. The operation wire 13 slidably penetrates through the slider 22, guided by the support member 23 of the operation body 21, and is securely fixed to the support member by an appropriate means such as caulking or adhesion.

As shown in FIGS. 3 to 8, the support member 23 of the operation body 21 is formed in a flat configuration in which the dimension in the lateral direction is smaller than the dimension in the vertical direction in FIGS. 3 and 4. In addition, the through-window 34 and the opening of the portion 37 are oriented in one same direction, and both are opened in both opposed side surfaces. Lightening portions 55 necessary for molding are formed at appropriate positions in the support member 23. The support member 23 is formed in a flat structure in which both side surface portions are substantially flat and the dimension in the lateral direction is smaller than the dimension in the vertical direction. The left and right portions of the finger flanges 48 and 49 of the slider 22 are cut away so that side flat surface portions opposed to each other are formed. Therefore, the entire operation portion 12 including the operation body 21 and the slider 22 is formed in a flat structure in which the dimension thereof in the lateral direction is smaller than the dimension thereof in the vertical direction.

Figure 9:
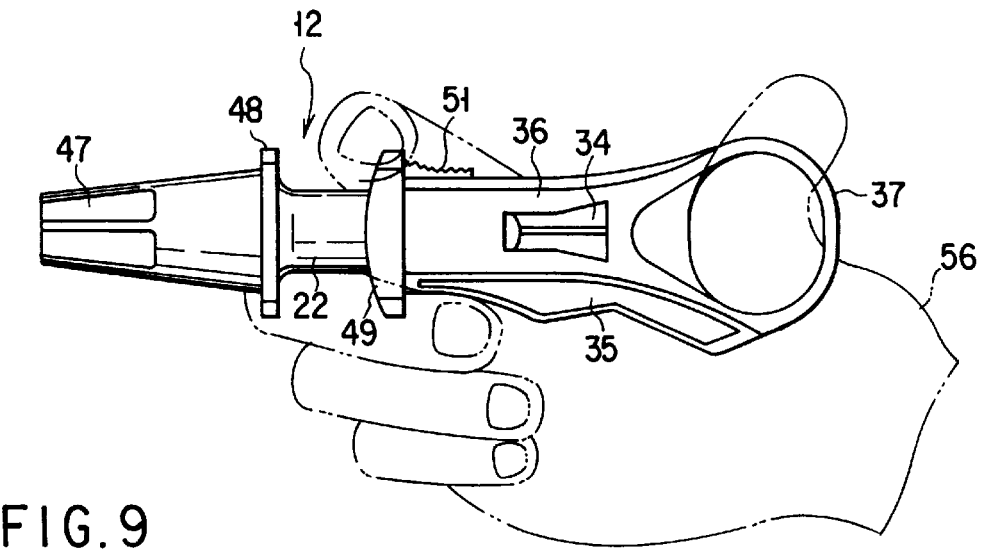
FIG. 9 is a view explaining an operation method of the operation portion of the forceps according to the first embodiment.

In the following, the operation method of the operation portion 12 of the forceps 10 will be explained. Two methods described are applicable as the operation method, i.e., the driving operation for driving the basket portion 14. The first operation method is carried out with a gripping type action as shown in FIG. 9. Specifically, the thumb of an operator's hand 56 is inserted into the ring-like finger engaging portion 37 of the operation body 21, and the portion between the pair of front and rear finger flanges 48 and 49 is clamped between other fingers of the hand 56, e.g., between the forefinger and the middle finger. Further, the slider 22 is slid in the axial direction by the thumb, so that the operation wire 13 is moved in relation to the sheath 11 and the basket portion 14 is extended from the distal end portion of the sheath 11. In this manner, the elastic wires 15 are shaped to have a large diameter. A stone is grasped in the basket portion 14 through a clearance between the elastic wires 15, and thereafter, the basket portion 14 is retracted into the sheath 11, thereby tightening the elastic wires 15 and grasping the stone. In this operation method, the thumb of the hand 56 is inserted into the ring-like portion 37 so that the thumb is securely held by the ring 37 and the operator scarcely drops the portion 12, i.e., the forceps 10 for an endoscope. Therefore, the operation can be done safely with reliability.

Figure 10:
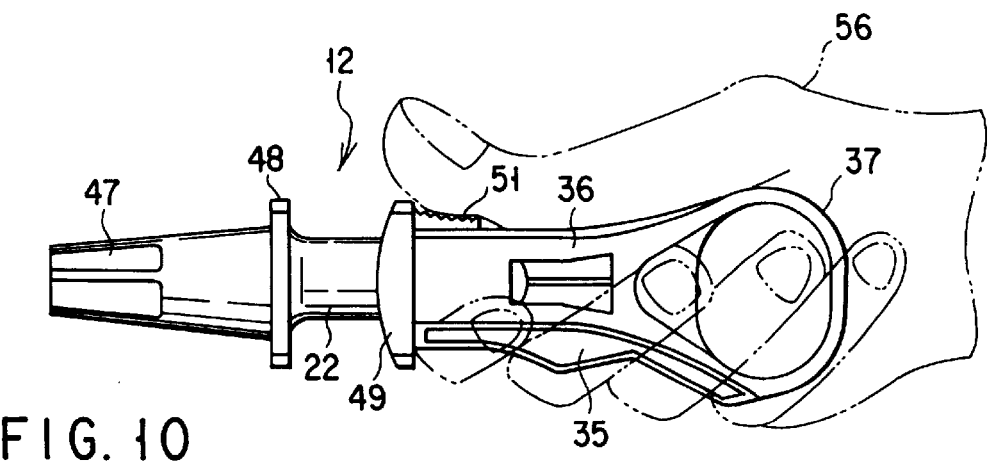
FIG. 10 is a view explaining another operation method of the operation portion of the forceps according to the first embodiment.

The second method is carried out with a grasping type action as shown in FIG. 10. Specifically, an operator grasps the grip portion 36 of the operation body 21 by the palm of his or her one hand 56, and hangs the thumb of the hand 56 on the finger hang portion 51 of the slider 22, thus grasping the operation portion 12. Further, the operation wire 13 is moved in the axial direction in relation to the sheath 11 by sliding the slider 22 in the forward and backward directions, thereby to extend the basket portion 14 from the distal end of the sheath 11. Thereafter, a stone is picked up into the basket portion 14 through a clearance between the elastic wires 15 expanded widely. Thereafter, the basket portion 14 is retracted into the sheath 11, thereby tightening the basket portion 14 and grasping the stone. In this operation method, the portion of the grip portion 36 of the operation body 21 is grasped by the hand 56 and the slider 22 is operated by the thumb of the hand. It is therefore possible to obtain a clear feeling of operation.

Thus, according to the forceps 10 of the present embodiment, either one of two operation methods can be selected in accordance with an operator's choice and a situation of a medical operation. In addition, finger rest portion 51 of the slider 22 further extends toward the rear end portion from the finger flange 49 in the rear end portion. Accordingly, it is possible to enlarge the operation stroke for operating the slider 22 by the thumb of the hand 56 which grasps the support member 23 of the operation body 21.

In addition, the operation portion 12 of the forceps 10 is formed generally in a flat shape, and therefore, can be stably set on a table. In addition, the forceps 10 can be packed in a sterilizing package (or packing case) and is widely and compact to stock.

On the contrary, the support member 23 of the operation body 21 and the finger flanges 48 and 49 of the slider 22 can be rounded over the entire circumferences.

Second Embodiment

Figure 11:
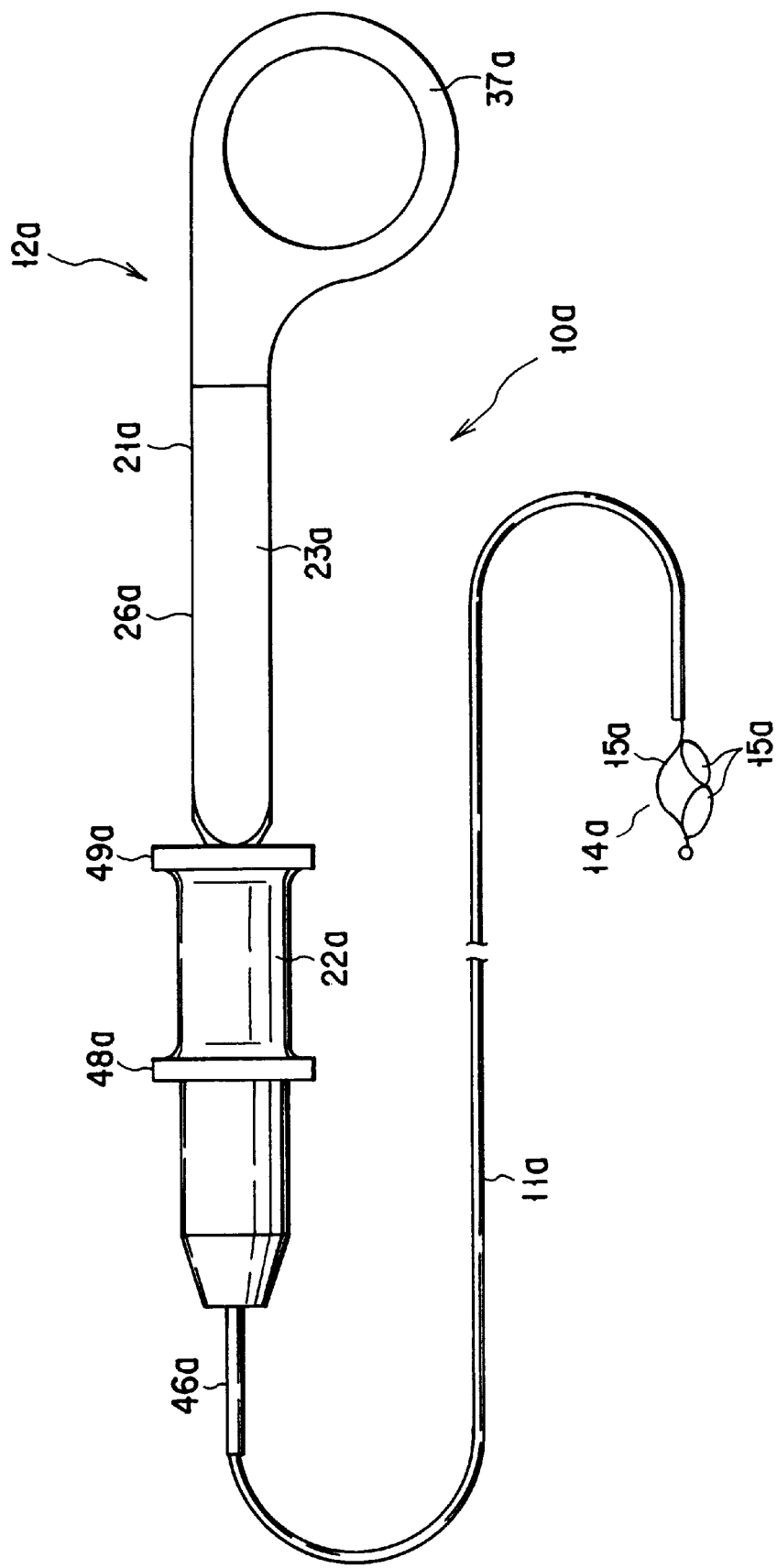
FIG. 11 is a side view of a forceps for an endoscope according to a second embodiment of the present invention.

A forceps 10a according to a second embodiment of the present invention will be explained with reference to FIG. 11.

The forceps 10a differs from the forceps 10 according to the first embodiment described above, in the following points. At first, the support member 23a of the operation body 21a is formed in a rod-like structure having a circular cross-section. In addition, the ring-like finger engaging portion 37a formed at the rear end portion of the operation body 21a is provided such that the center of the portion 37a is deviated downwards in the figure in relation to the longitudinal axis of the support member 23a. By thus providing the finger engaging portion 37a deviated downwards in relation to the grip portion 36a, operation is facilitated when the thumb of an operation is inserted in the finger engaging portion 37a. Further, if the operation body 21a and the slider 22a are arranged to be rotatable in relation to each other, operation of rotating the basket portion 14a by the operation wire can be facilitated by rotating the operation body 21a in relation to the slider 22a.

In the above first embodiment, the finger rest portion 51 is provided at the hood portion extending from the flange 49 of the slider 22. In contrast, the present embodiment is not provided with such a hood portion. The flange 49a at the rear end portion also serves as a finger rest portion to be fitted with the thumb of an operator. A slip stopper should preferably formed at the portion of the rear flange 49a.

In addition, each of the finger flanges 48a and 49a of the slider 22a may be formed a flat structure like in the first embodiment, or may be formed in a structure having a circular cross-section.

Third Embodiment

Figure 12:
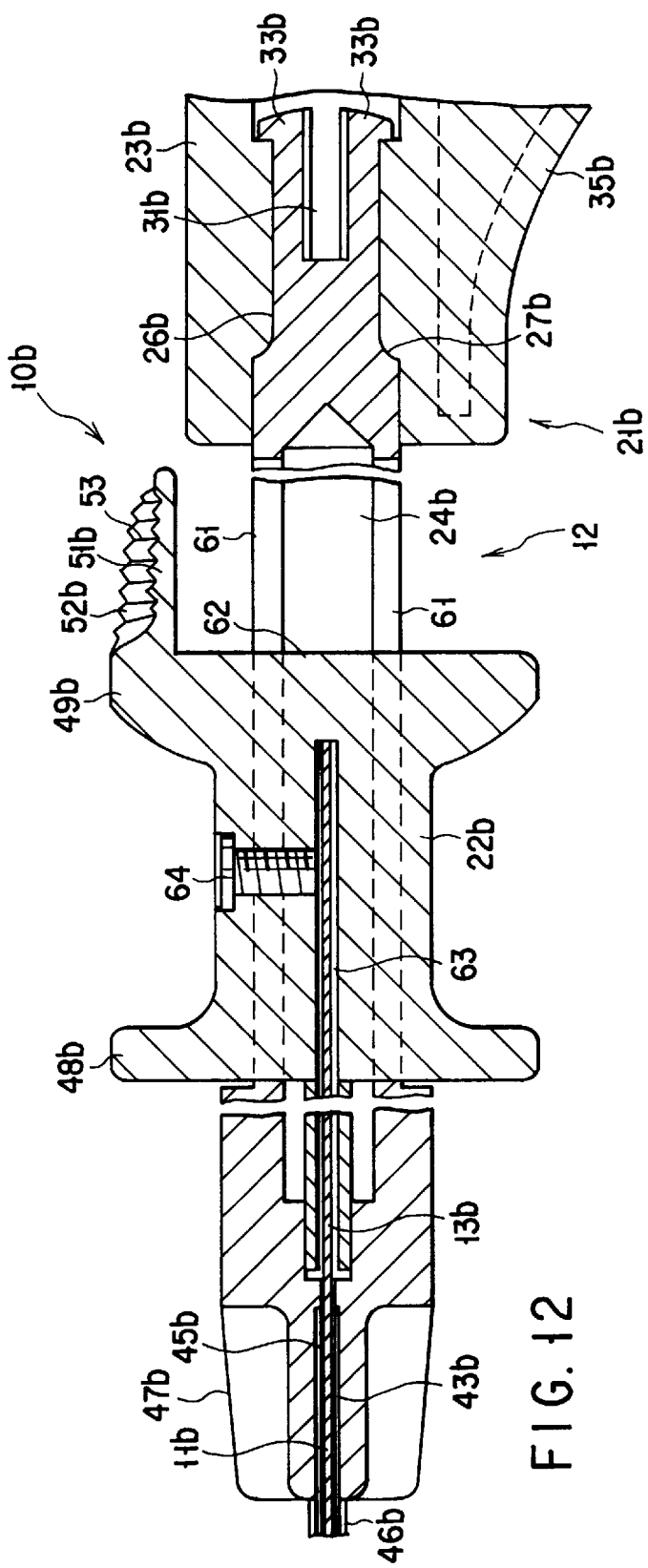
FIG. 12 is a longitudinal cross-sectional view of an operation portion of a forceps for an endoscope according to a third embodiment.

A forceps 10b according to a third embodiment of the present invention will be explained with reference to FIG. 12. The forceps 10b differs from the forceps 10 of the first embodiment, in the following points.

The slider 22b is slidably attached to the guide member 24b of the operation body 21b. Therefore, a guide slit 61 along the axial direction is formed in the guide member 24b. Further, a portion 62 to be engaged in the guide slit 61 is formed on the slider 22b. A hole 63 in which the rear end portion of the operation wire 13 is fitted is provided in the portion 62 of the slider 22b. The rear end portion of the operation wire 13b is inserted into the hole 63 and is fixed by tightening a fixing screw 64. Meanwhile, the guide member 24b of the operation body 21b is further extended over the slider 22b toward the distal end portion. The proximal end portion of the sheath 11b is fixed to the extended distal end portion of the guide member 24b.

In the present embodiment, the base end portion of the operation wire 13b is fixed not to the operation body 21b but to slider 22b. In addition, the sheath 11b is fixed to the operation body 21b. In this case, the sheath 11b and the operation wire 13b can be relatively moved along the axial direction, like in the first embodiment. The other components than described above are the same as those of the forceps 10 according to the first embodiment.

Fourth Embodiment

Figure 13:
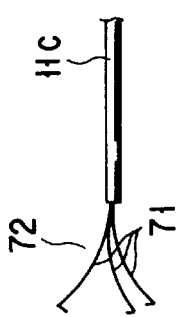
FIG. 13 is a side view of a top end portion of a forceps for an endoscope according to a fourth embodiment.
Figure 14:
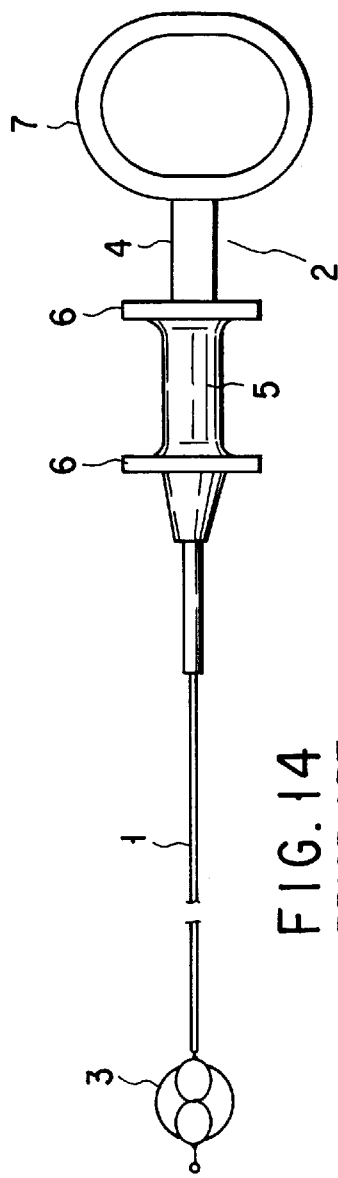
FIG. 14 is a side of a conventional type of a forceps for an endoscope.

Each of the embodiments described above relates to a basket type forceps. However, in the fourth embodiment, the grasp portion 72 is formed by three grasp pieces 71, as shown in FIG. 13. The grasp portion 72 can be opened and closed by moving the operation wire in relation to the sheath 11c. The other components of the present embodiment are the same as those of the first embodiment.

Note that the present invention is not limited to a forceps but is applicable to various treatment tools for an endoscope, such as a high-frequency snare and the like.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment tool usable under observation through an endoscope, said treatment tool comprising:

a treatment portion provided at a distal end portion of the treatment tool;

an insertion portion for inserting the treatment portion into a body cavity;

first and second operation members each having a distal end portion and a proximal end portion and being movable relatively to each other, the operation members being provided at a proximal end portion of the insertion portion and forming an operation portion by which an operator can drive and operate the treatment portion from outside of a human body;

a first finger engaging portion formed on the proximal end portion of the first operation member and having a ring-like shape into which the operator can insert his or her thumb;

a grip portion formed on the first operation member adjacent to the first finger engaging portion such that the operator can grasp the grip portion using his or her palm;

a second finger engaging portion formed on the second operation member such that the operator can engage the second finger engaging portion with at least one finger of the same hand whose thumb engages the first finger engaging portion; and a third finger engaging portion formed on the second operation member such that the operator can engage the third finger engaging portion with his or her thumb of the same hand whose palm grasps the grip portion;

wherein selection can be made between a first drive operation of relatively moving the first and second operation members using the first and second finger engaging portions, and a second drive operation of relatively moving the first and second operation members using the grip portion and the third finger engaging portion;

wherein the second operation member is axially slidable relative to the first operation member and is provided closer to the distal end portion of the treatment tool than the first operation member; and wherein the second finger engaging portion comprises a pair of flanges.

2. A treatment tool according to claim 1, wherein the third finger engaging portion is formed at one of the pair of flanges.

3. A treatment tool according to claim 1, wherein the third finger engaging portion is provided closer to the grip portion than the second finger engaging portion.

4. A treatment tool according to claim 1, wherein the first and second operation members have respective substantially flat side surface portions opposed to each other, by which the operation portion is formed into a generally flat shape.

5. A treatment tool according to claim 1, wherein each of the flanges of the second finger engaging portion has substantially flat side surface portions opposed to each other.

6. A treatment tool usable under observation through an endoscope, said treatment tool comprising:

a treatment portion provided at a distal end portion of the treatment tool;

an insertion portion for inserting the treatment portion into a body cavity;

first and second operation members each having a distal end portion and a proximal end portion and being movable relatively to each other, the operation members being provided at a proximal end portion of the insertion portion and forming an operation portion by which an operator can drive and operate the treatment portion from outside of a human body;

a first finger engaging portion formed on the proximal end portion of the first operation member and having a ring-like shape into which the operator can insert his or her thumb;

a grip portion formed on the first operation member adjacent to the first finger engaging portion such that the operator can grasp the grip portion using his or her palm;

a second finger engaging portion formed on the second operation member such that the operator can engage the second finger engaging portion with at least one finger of the same hand whose thumb engages the first finger engaging portion; and a third finger engaging portion formed on the second operation member such that the operator can engage the third finger engaging portion with his or her thumb of the same hand whose palm grasps the grip portion;

wherein selection can be made between a first drive operation of relatively moving the first and second operation members using the first and second finger engaging portions, and a second drive operation of relatively moving the first and second operation members using the grip portion and the third finger engaging portion;

wherein the second finger engaging portion comprises a pair of flanges provided at the second operation member; and wherein the third finger engaging portion comprises a hood portion extending toward the grip portion from the one of the pair of flanges that is closest to the grip portion.

7. A treatment tool usable under observation through an endoscope, said treatment tool comprising:

a treatment portion provided at a distal end portion of the treatment tool;

an insertion portion for inserting the treatment portion into a body cavity;

first and second operation members each having a distal end portion and a proximal end portion and being movable relatively to each other, the operation members being provided at a proximal end portion of the insertion portion and forming an operation portion by which an operator can drive and operate the treatment portion from outside of a human body;

a first finger engaging portion formed on the proximal end portion of the first operation member and having a ring-like shape into which the operator can insert his or her thumb;

a grip portion formed on the first operation member adjacent to the first finger engaging portion such that the operator can grasp the grip portion using his or her palm;

a second finger engaging portion formed on the second operation member such that the operator can engage the second finger engaging portion with at least one finger of the same hand whose thumb engages the first finger engaging portion; and a third finger engaging portion formed on the second operation member such that the operator can engage the third finger engaging portion with his or her thumb of the same hand whose palm grasps the grip portion;

wherein selection can be made between a first drive operation of relatively moving the first and second operation members using the first and second finger engaging portions, and a second drive operation of relatively moving the first and second operation members using the grip portion and the third finger engaging portion;

wherein the grip portion comprises an extended portion on which a finger may be rested;

wherein the second operation member is axially slidable relative to the first operation member and is provided closer to the distal end portion of the treatment tool than the first operation member; and wherein the second finger engaging portion comprises a pair of flanges.

8. A treatment tool usable under observation by an endoscope, said treatment tool comprising:

a sheath having a distal end portion to be inserted into a body cavity;

an operation wire inserted in the sheath such that the operation wire is movable in an axial direction;

a treatment portion provided at a distal end portion of the operation wire, which can be driven and moved between a first position where the treatment portion is extended from a distal end of the sheath and a second position where the treatment portion is retracted into the sheath;

first and second operation members each having a distal end portion and a proximal end portion and being movable relatively to each other, one of the first and second operation members being connected to the sheath and the other one of the first and second operation members being connected to the operation wire, such that the first and second operation members form an operation portion to be operated by the operator to drive and move the treatment portion between the first and second positions;

a first finger engaging portion formed on the proximal end portion of the first operation member and having a ring-like shape into which the operator can insert his or her thumb;

a grip portion formed on the first operation member adjacent to the first finger engaging portion such that the operator can grasp the grip portion using his or her palm;

a second finger engaging portion formed on the second operation member such that the operator can engage the second finger engaging portion with at least one finger of the same hand whose thumb engages the first finger engaging portion;

a third finger engaging portion formed on the second operation member such that the operator can engage the third finger engaging portion with his or her thumb of the same hand whose palm grasps the grip portion; and wherein selection can be made between a first drive operation of relatively moving the first and second operation members using the first and second finger engaging portions, and a second drive operation of relatively moving the first and second operation members using the grip portion and the third finger engaging portion;

wherein the second operation member is axially slidable relative to the first operation member and is provided closer to a distal end portion of the treatment tool than the first operation member; and wherein the second finger engaging portion comprises a pair of flanges.

9. A treatment tool according to claim 8, wherein the third finger engaging portion is formed at one of the pair of fingers.

10. A treatment tool according to claim 8, wherein the third finger engaging portion is provided closer to the grip portion than the second finger engaging portion.

11. A treatment tool according to claim 8, wherein the first and second operation members have respective substantially flat side surface portions opposed to each other, by which the operation portion is formed into a generally flat shape.

12. A treatment tool according to claim 8, wherein each of the flanges of the second finger engaging portion has substantially flat side surface portions opposed to each other.

13. A treatment tool according to claim 8, wherein the grip portion comprises an extending portion on which a finger may be rested.

14. A treatment tool according to claim 8, wherein the first operation member is connected to the operation wire and the second operation member is connected to the sheath.

15. A treatment tool according to claim 8, wherein the first operation member is connected to the sheath and the second operation member is connected to the operation wire.

16. A treatment tool usable under observation by an endoscope, said treatment tool comprising:

a sheath having a distal end portion to be inserted into a body cavity;

an operation wire inserted in the sheath such that the operation wire is movable in an axial direction;

a treatment portion provided at a distal end portion of the operation wire, which can be driven and moved between a first position where the treatment portion is extended from a distal end of the sheath and a second position where the treatment portion is retracted into the sheath;

first and second operation members each having a distal end portion and a proximal end portion and being movable relatively to each other, one of the first and second operation members being connected to the sheath and the other one of the first and second operation members being connected to the operation wire, such that the first and second operation members form an operation portion to be operated by the operator to drive and move the treatment portion between the first and second positions;

a first finger engaging portion formed at the proximal end portion of the first operation member and having a ring-like shape into which the operator can insert his or her thumb;

a grip portion formed at the first operation member adjacent to the first finger engaging portion such that the operator can grasp the grip portion using his or her palm;

a second finger engaging portion formed at the second operation member such that the operator can engage the second finger engaging portion with at least one finger of the same hand whose thumb engages the first finger engaging portion;

a third finger engaging portion formed at the second operation member such that the operator can engage the third finger-hang portion with his or her thumb of the same hand whose palm grasps the grip portion;

wherein selection can be made between a first drive operation of relatively moving the first and second operation members using the first and second finger engaging portions, and a second drive operation of relatively moving the first and second operation members using the grip portion and the third finger engaging portion;

wherein the second finger engaging portion comprises a pair of flanges provided at the second operation member; and wherein the third finger engaging portion comprises a hood portion extending toward the grip portion from the one of the pair of flanges that is closest to the grip portion.

17. A treatment tool usable under observation by an endoscope, said treatment tool comprising:

a sheath having a distal end portion to be inserted into a body cavity;

an operation wire inserted in the sheath such that the operation wire is movable in an axial direction;

a treatment portion provided at a distal end portion of the operation wire, which can be driven and moved between a first position where the treatment portion is extended from a distal end of the sheath and a second position where the treatment portion is retracted into the sheath;

first and second operation members each having a distal end portion and a proximal end portion and being movable relatively to each other, one of the first and second operation members being connected to the sheath and the other one of the first and second operation members being connected to the operation wire, such that the first and second operation members form an operation portion to be operated by the operator to drive and move the treatment portion between the first and second positions;

a first finger engaging portion formed at the proximal end portion of the first operation member and having a ring-like shape into which the operator can insert his or her thumb;

a grip portion formed at the first operation member adjacent to the first finger engaging portion such that the operator can grasp the grip portion using his or her palm;

a second finger engaging portion formed at the second operation member such that the operator can engage the second finger engaging portion with at least one finger of the same hand whose thumb engages the first finger engaging portion;

a third finger engaging portion formed at the second operation member such that the operator can engage the third finger-hang portion with his or her thumb of the same hand whose palm grasps the grip portion;

wherein selection can be made between a first drive operation of relatively moving the first and second operation members using the first and second finger engaging portions, and a second drive operation of relatively moving the first and second operation members using the grip portion and the third finger engaging portion;

wherein the grip portion comprises an extending portion on which a finger may be rested; and wherein the extending portion has a wavy outer shape.

18. A treatment tool usable under observation by an endoscope, said treatment tool comprising:

a sheath having a distal end portion to be inserted into a body cavity;

an operation wire inserted in the sheath such that the operation wire is movable in an axial direction;

a treatment portion provided at a distal end portion of the operation wire, which can be driven and moved between a first position where the treatment portion is extended from a distal end of the sheath and a second position where the treatment portion is retracted into the sheath;

first and second operation members each having a distal end portion and a proximal end portion and being movable relatively to each other, one of the first and second operation members being connected to the sheath and the other one of the first and second operation members being connected to the operation wire, such that the first and second operation members form an operation portion to be operated by the operator to drive and move the treatment portion between the first and second positions;

a first finger engaging portion formed at the proximal end portion of the first operation member and having a ring-like shape into which the operator can insert his or her thumb;

a grip portion formed at the first operation member adjacent to the first finger engaging portion such that the operator can grasp the grip portion using his or her palm;

a second finger engaging portion formed at the second operation member such that the operator can engage the second finger engaging portion with at least one finger of the same hand whose thumb engages the first finger engaging portion;

a third finger engaging portion formed at the second operation member such that the operator can engage the third finger-hang portion with his or her thumb of the same hand whose palm grasps the grip portion;

wherein selection can be made between a first drive operation of relatively moving the first and second operation members using the first and second finger engaging portions, and a second drive operation of relatively moving the first and second operation members using the grip portion and the third finger engaging portion;

wherein the grip portion comprises an extending portion on which a finder may be rested; and wherein the grip portion has a predetermined size in a lateral direction, and the extending portion has a size in the lateral direction which is smaller than the predetermined size of the grip portion.

* * * * *